US010912484B2

(12) United States Patent
Ziv-Ari et al.

(10) Patent No.: US 10,912,484 B2
(45) Date of Patent: Feb. 9, 2021

(54) MULTIPLEXING OF HIGH COUNT ELECTRODE CATHETER(S)

(71) Applicant: Biosense Webster (Israel) Ltd., Yokneam (IL)

(72) Inventors: Morris Ziv-Ari, Atlit (IL); Yoav Benaroya, Kfar Saba (IL); Roy Urman, Karkur (IL); Oded Baron, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 83 days.

(21) Appl. No.: 16/030,358

(22) Filed: Jul. 9, 2018

(65) Prior Publication Data

US 2020/0008705 A1    Jan. 9, 2020

(51) Int. Cl.
| | |
|---|---|
| *A61B 5/05* | (2006.01) |
| *A61B 5/0536* | (2021.01) |
| *A61B 5/042* | (2006.01) |
| *A61B 5/00* | (2006.01) |
| *A61B 18/14* | (2006.01) |
| *G01N 27/07* | (2006.01) |
| *A61B 18/00* | (2006.01) |

(52) U.S. Cl.
CPC .......... *A61B 5/0536* (2013.01); *A61B 5/0422* (2013.01); *A61B 5/6859* (2013.01); *A61B 18/1492* (2013.01); *G01N 27/07* (2013.01); *A61B 2018/00351* (2013.01); *A61B 2018/00577* (2013.01)

(58) Field of Classification Search
CPC ............ A61B 5/06; A61B 5/063; A61B 5/065
See application file for complete search history.

(56) References Cited

U.S. PATENT DOCUMENTS

| | | | |
|---|---|---|---|
| 5,391,199 | A | 2/1995 | Ben-Haim |
| 6,049,732 | A | 4/2000 | Panescu et al. |
| 6,226,547 | B1 | 5/2001 | Lockhart et al. |
| 6,239,724 | B1 | 5/2001 | Doron et al. |
| 6,301,496 | B1 | 10/2001 | Reisfeld |
| 6,332,089 | B1 | 12/2001 | Acker et al. |
| 6,484,118 | B1 | 11/2002 | Govari |

(Continued)

FOREIGN PATENT DOCUMENTS

| | | |
|---|---|---|
| EP | 0499491 A2 | 8/1992 |
| WO | 199605768 A1 | 2/1996 |
| WO | 2017/024107 A1 | 2/2017 |

OTHER PUBLICATIONS

Extended European Search Report dated Nov. 13, 2019 for the European Patent Application No. 19184969.4.

*Primary Examiner* — Michael J D Abreu (57) ABSTRACT

A method is disclosed comprising: performing a first scan of an organ using a set of electrodes in a catheter that are currently active; deactivating one or more of the electrodes in the set based on data that is collected as a result of the first scan; tuning the set by at least one of (i) deactivating one or more electrodes in the set that remain active after the deactivating, and (ii) activating one or more electrodes in the catheter that are inactive; performing a second scan of the organ using electrodes in the set that are currently active after the tuning is performed, and generating a map of the organ based on data collected as a result of the second scan; and outputting the map of the organ for presentation to a user.

20 Claims, 9 Drawing Sheets

(56) References Cited

U.S. PATENT DOCUMENTS

| | | |
|---|---|---|
| 6,618,612 B1 | 9/2003 | Acker et al. |
| 6,690,963 B2 | 2/2004 | Ben-Haim et al. |
| 6,748,255 B2 | 6/2004 | Fuimaono et al. |
| 6,892,091 B1 * | 5/2005 | Ben-Haim ............ A61B 5/0422 600/509 |
| 7,536,218 B2 | 5/2009 | Govari et al. |
| 7,729,742 B2 | 6/2010 | Govari |
| 7,756,576 B2 | 7/2010 | Levin |
| 8,103,327 B2 | 1/2012 | Harlev et al. |
| 2004/0068178 A1 | 4/2004 | Govari |
| 2004/0220637 A1 | 11/2004 | Zdeblick et al. |
| 2005/0033136 A1 | 2/2005 | Govari et al. |
| 2006/0009690 A1 | 1/2006 | Fuimaono et al. |
| 2015/0057529 A1 | 2/2015 | Merschon et al. |
| 2015/0366467 A1 * | 12/2015 | De Kock ............ A61N 1/36117 600/377 |
| 2016/0228023 A1 | 8/2016 | Govari |

* cited by examiner

MULTIPLEXING OF HIGH COUNT ELECTRODE CATHETER(S)

SUMMARY

Catheterization is a medical procedure used to diagnose and treat various conditions. During catheterization, a catheter is inserted into a patient's organ through the patient's veins or arteries. The catheter may be a thin tube having electrodes on one end and a handle and a connector on the other. The connector may be plugged into a diagnostic device which processes signals received from the electrodes to provide useful diagnostic information to doctors and other medical professionals.

According to one aspect of the disclosure, a method is provided comprising: performing a first scan of an organ using a set of electrodes in a catheter that are currently active; deactivating one or more of the electrodes in the set based on data that is collected as a result of the first scan; tuning the set by at least one of (i) deactivating one or more electrodes in the set that remain active after the deactivating, and (ii) activating one or more electrodes in the catheter that are inactive; performing a second scan of the organ using electrodes in the set that are currently active after the tuning is performed, and generating a map of the organ based on data collected as a result of the second scan; and outputting the map of the organ for presentation to a user.

According to another aspect of the disclosure, a diagnostic device is provided, comprising: an output device; and at least one processor operatively coupled to the output device, the at least one processor being configured to: perform a first scan of an organ using a set of electrodes in a catheter that are currently active; deactivate one or more of the electrodes in the set based on data that is collected as a result of the first scan; tune the set by at least one of (i) deactivating one or more electrodes in the set that remain active after the deactivating, and (ii) activating one or more electrodes in the catheter that are inactive; perform a second scan of the organ using electrodes in the set that are currently active after the tuning is performed, and generating a map of the organ based on data collected as a result of the second scan; and output the map of the organ using the output device.

BRIEF DESCRIPTION OF THE DRAWINGS

The following detailed description of the embodiments of the present invention will be better understood when read in conjunction with the appended drawings. For the purpose of illustration, there are shown in the drawings embodiments which are presently preferred. It is understood, however, that the invention is not limited to the precise arrangements and instrumentalities shown. In the drawings.

DETAILED DESCRIPTION OF THE PREFERRED EMBODIMENTS

According to aspects of the disclosure, an imaging system is disclosed that includes a diagnostic device and a catheter. The catheter may include a large number of electrodes (e.g., approximately 200) that are coupled to the diagnostic device via switching circuitry. The catheter may be used to examine a patient's organ, such as a heart, lungs, or kidneys. The diagnostic device may be configured to focus the electrodes in the catheter on specific regions of interest in the patient's organ. Focusing the electrodes in the catheter may include one or more of, deactivating electrodes that are not in proximity to the regions of interest, activating additional electrodes that are in proximity to the regions of interest, and/or deactivating redundant electrodes that are situated in proximity to the regions of interest. Examples of different processes for activating and/or deactivating electrodes in a catheter in order to focus the electrodes in the catheter on specific regions of interest in a patient's organ are provided further below.

Figure 1A:
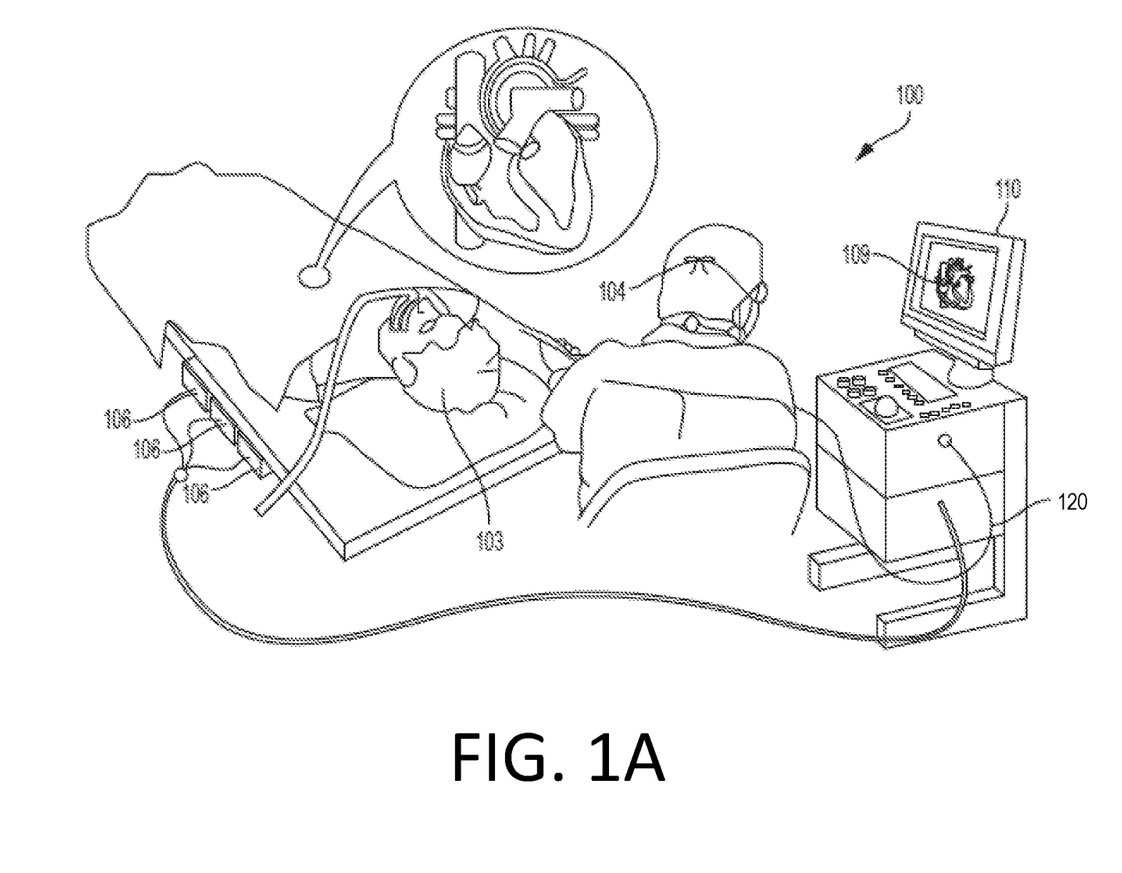
FIG. 1A is a diagram illustrating the operation of a system for performing electro-anatomic mapping, according to aspects of the disclosure.

FIG. 1A is a diagram of a system 100 including a diagnostic device 110 that is coupled to a catheter 120. In the present example, the catheter 120 is a lasso catheter. However, it will be understood that alternative implementations are possible in which the catheter 120 is any another suitable type of catheter, such as a basket catheter for example. In operation of the system 100, a physician 104 may thread the catheter 120 through an artery or vein of a patient 103 to a destination which is desired to be examined with the catheter 120, such as a particular organ of the patient. After the catheter 120 has reached its destination, the diagnostic device 110 may receive signals from electrodes and/or other sensors that are part of the catheter. The diagnostic device 110 may then amplify, filter, digitize, and combine those signals to generate a map of the patient's organ. The map may be a 2D image of the patient's organ, a 3D image of the patient's organ, and/or any other suitable type of electroanatomic map of the patient's organ. The catheter 120 may be used to scan various organs of the patient 103, such as the patient's lung, the patient's kidneys, and/or any suitable type of organ.

Figure 1B:
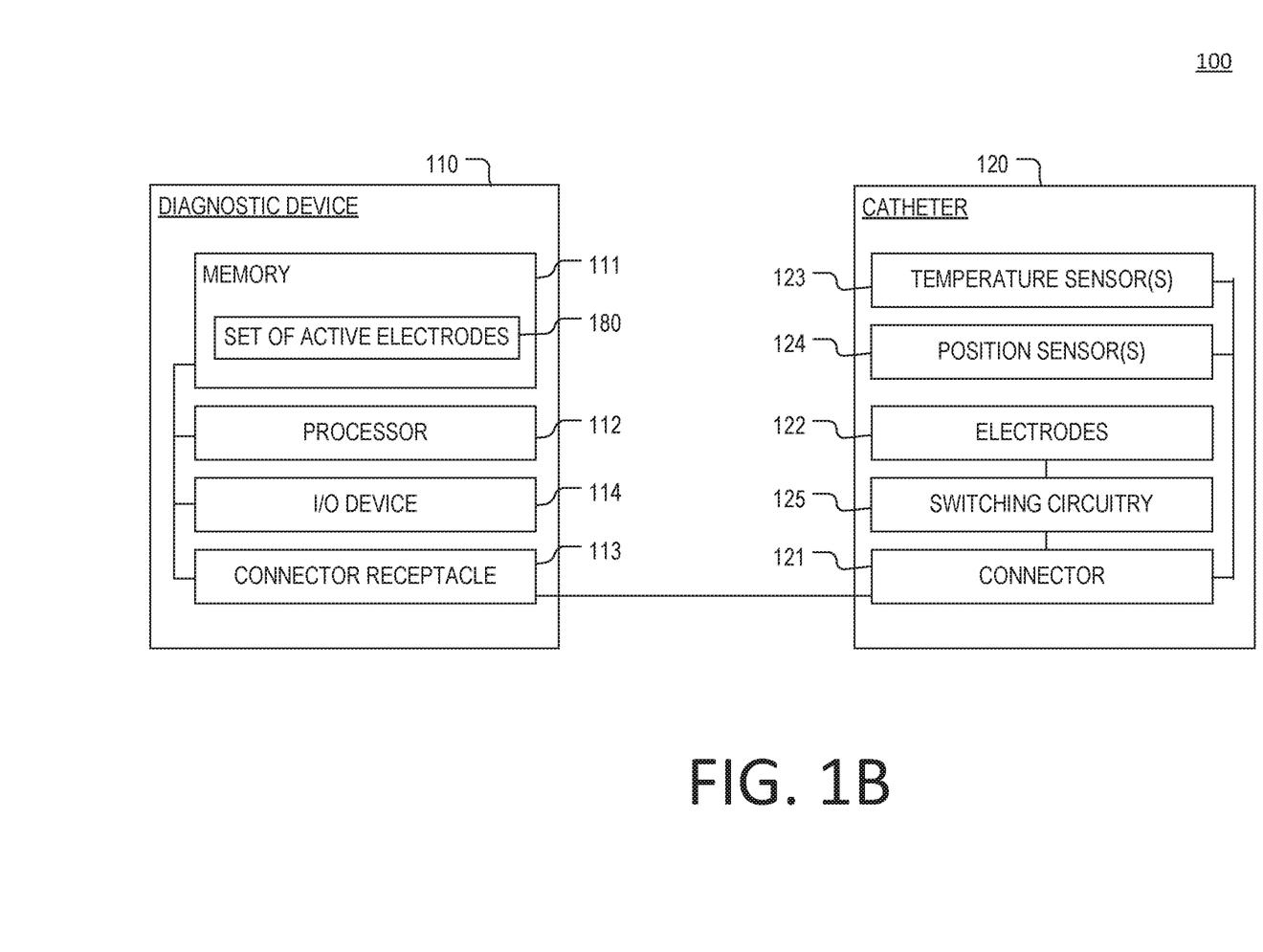
FIG. 1B is a schematic diagram of the system of FIG. 1A, according to aspects of the disclosure.

FIG. 1B is a schematic diagram of the system 100, according to aspects of the disclosure. As illustrated, the diagnostic device 110 may include a memory 111, a processor 112, a connector receptacle 113, and an input-output (I/O) device 114. Any of the memory 111, the connector receptacle 113, and the I/O device 114 may be operatively coupled to the processor via a system bus or another similar device.

The memory 111 may include any suitable type of volatile or non-volatile memory, such as random-access memory (RAM), a flash memory, a solid-state drive (SSD), a hard drive (HD), a dynamic random-access memory (DRAM), and/or erasable programmable read-only memory (EPROM). In some implementations, the memory 111 may store a data structure 180. The data structure 180 may identify a list of electrodes in the catheter 120 that are currently active. According to the present disclosure, when an electrode is activated, one or more signals generated by the electrode in a subsequent scan of a patient's organ are used to generate a map of the patient's organ. According to the present disclosure, when an electrode is deactivated, signals generated by the electrode are not used to generate a map of the patient's organ when a scan of the organ is subsequently performed. The data structure 180 is discussed further below with respect to FIG. 1D.

The processor 112 may include one or more of a general-purpose processor (e.g., an x86 processor, a MIPS processor, a RISC processor, etc.), an application-specific integrated circuit (ASIC), a field-programmable gate array (FPGA), a complex programmable logic device (CPLD), a controller, and/or any other suitable type of processing circuitry. The connector receptacle 113 may include any suitable type of receptacle for receiving the connector 121 of the catheter 120. The input/output device 114 may include one or more of a display, a touchpad, a mouse, a keyboard, a microphone, a camera, a printer, a speaker, and/or any other suitable type of I/O device.

The catheter 120 may include a connector 121, electrodes 122, temperature sensors 123, position sensors 124, and a switching circuitry 125. The connector 121 may include any suitable type of connector for plugging the catheter 120 into the diagnostic device 110. The electrodes 122 may include one or more mapping electrodes for measuring electro-cardiac signals at one or more respective contact points with the patient's heart tissue. Additionally or alternatively, in some implementations, the electrodes 122 may include one or more ablation electrodes and/or one or more electrodes that are capable of performing both mapping and ablation. The position sensors 124 may be disposed near a distal end of the catheter 120. The position sensors 124 may interact with magnetic field generators 106 disposed under the patient 103 (shown in FIG. 1A) to generate electric signals indicating the position of the catheter 120. In some implementations, such signals may be further used to detect the position (e.g., location and/or orientation) of individual electrodes in an organ that is being examined with the catheter 120.

The switching circuitry 125 may include any suitable type of electronic device (or devices) that is configured to select electrodes in the catheter 120 and route signals generated by the selected electrodes to the diagnostic device 110. In some implementations, the switching circuitry 125 may include one or more multiplexers that are arranged to form a switching fabric for addressing each (or at least some) of the electrodes 122 individually. Additionally or alternatively, in some implementations, the switching circuitry 125 may include one or more switches that are arranged to form a switching fabric for addressing each (or at least some) of the electrodes 122 individually. Stated succinctly, the present disclosure is not limited to any specific way for implementing the switching circuitry 125.

Figure 1C:
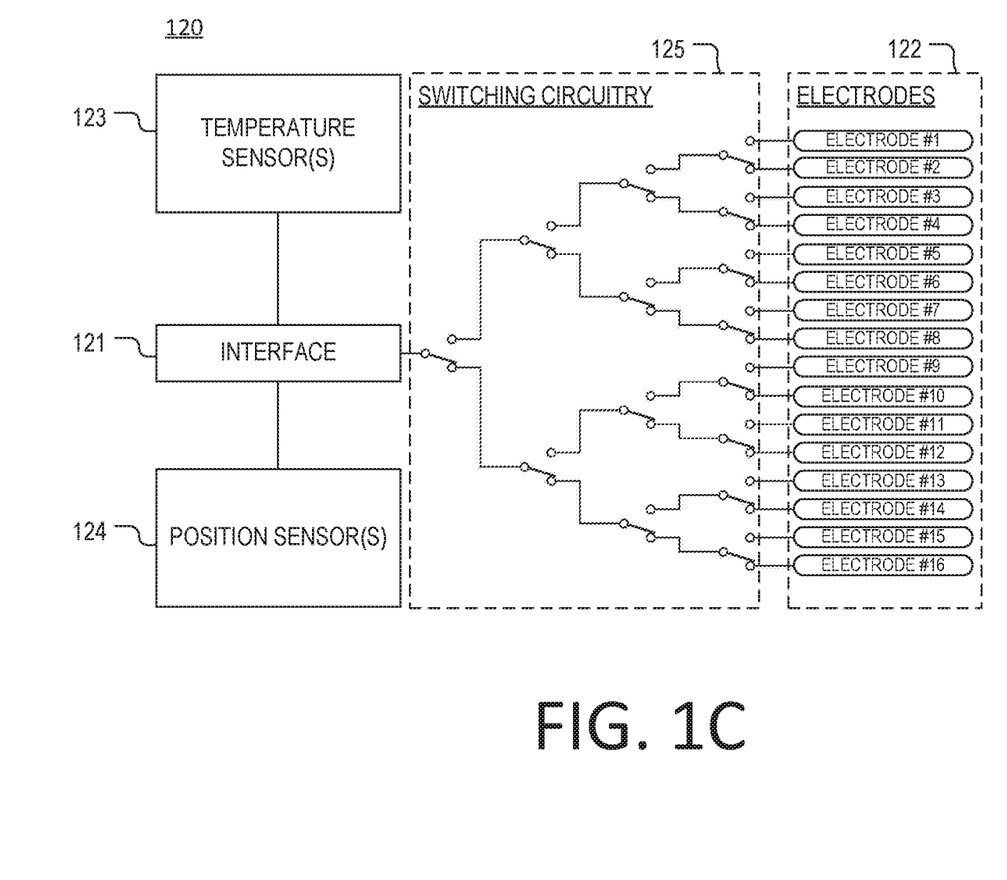
FIG. 1C is a diagram of an example of a catheter that is part of the system of FIG. 1A, according to aspects of the disclosure.

FIG. 1C is schematic diagram of the catheter 120 showing its structure in further detail. Although in the present example, the catheter 120 is depicted as including only 16 electrodes, it will be understood that the catheter 120 may include any suitable number of electrodes (e.g. 30, 50, 100, 200, 300, 500, 700, etc.)

Figure 1D:
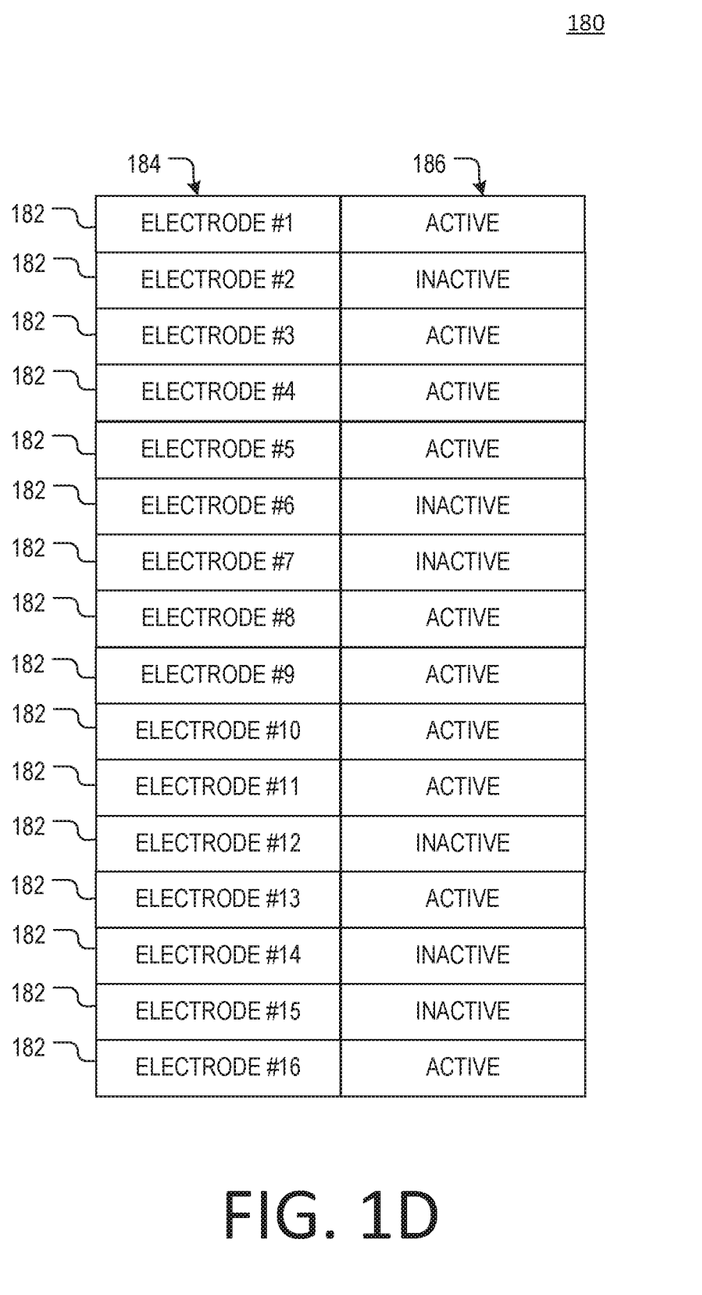
FIG. 1D is a diagram of an example of a data structure identifying a set of active electrodes in the catheter of FIG. 1C, according to aspects of the disclosure.

FIG. 1D is an example of a data structure 180 identifying a plurality of electrodes in the catheter that are currently active. The data structure may include a plurality of portions 182. Each portion 182 may include a respective identifier 184 of a different one of the electrodes 122, and a respective status identifier 186, which indicates whether the electrode is active or inactive. As discussed above, when a given electrode is active, signals generated by the given electrode during a scan of an organ are used (by the processor 112 of the diagnostic device 110) to generate a map of the organ. By contrast, when the given electrode is inactive, signals generated by the electrode are not used (by the processor 112 of the diagnostic device 110) in generating the map of the organ.

In some implementations, the processor 112 of the diagnostic device 110 may retrieve the data structure 180 from the memory 111 to determine which electrodes 122 in the catheter 120 are currently active. Afterwards, the diagnostic device 110 may generate a map of an organ that is scanned with the catheter 120 based only on signals generated by electrodes that are currently active. In some implementations, the diagnostic device 110 may not sample electrodes that are identified as being inactive. Additionally or alternatively, in some implementations, the diagnostic device 110 may sample and subsequently ignore (or discard) signals generated by electrodes that are identified as being inactive when the map is generated. Although in the present example electrodes are activated and deactivated by modifying the data structure 180, alternative implementations are possible in which inactive electrodes are enabled and disabled using the switching circuitry 125. In such implementations, inactive electrodes may be disconnected from the processor 112 (or the connector 121) using one or more switches that are part of the switching circuitry 125. Such switches may lie on an electrical path between an electrode and the processor 112 (or connector 112) and they may be configured to interrupt the electrical path when the electrode is disabled. The physical disconnecting of the inactive electrodes may be performed either in addition to or instead of the labeling of the inactive electrodes as such in the data structure 180 when the inactive electrodes are deactivated.

Although in the present example the data structure 180 is depicted as a table, the present disclosure is not limited to any specific way of implementing the data structure 180. Furthermore, although in the present example the portions 182 of the data structure 180 are encapsulated in the same data structure, alternative implementations are possible in which each portion 182 is implemented as a separate data structure. Stated succinctly, the present disclosure is not limited to any specific way of storing a respective indication for each of the electrodes 122 that indicates whether the electrode is active or inactive.

Furthermore, in the present example each electrode 122 is identified in the data structure 180 by using an ID corresponding to the electrode. However, alternative implementations are possible in which each of the electrodes is identified using an ID corresponding to a particular channel on which signals from the electrode are received. Additionally or alternatively, in some implementations, each of the electrodes may be identified using one or more identifiers that indicate the position of the electrode in the catheter 120. Additionally or alternatively, in some implementations, each of the electrodes can be identified using an address corresponding to the electrode that is used by the switching circuitry 125 to connect and/or disconnect the electrode 122 from the processor 112 (or connector 121). Stated succinctly, the present disclosure is not limited to any specific way of referencing the electrodes 122 in the catheter 120. The term identifier, as used throughout the specification, may refer to a number, a string, an alphanumerical string, and/or any other suitable type of identifier. By way of example, and depending on context, the term "signal" may refer to a waveform that is generated by an electrode and/or a digital representation of a characteristic of the waveform that is obtained by sampling and subsequently digitizing the waveform.

Figure 2:
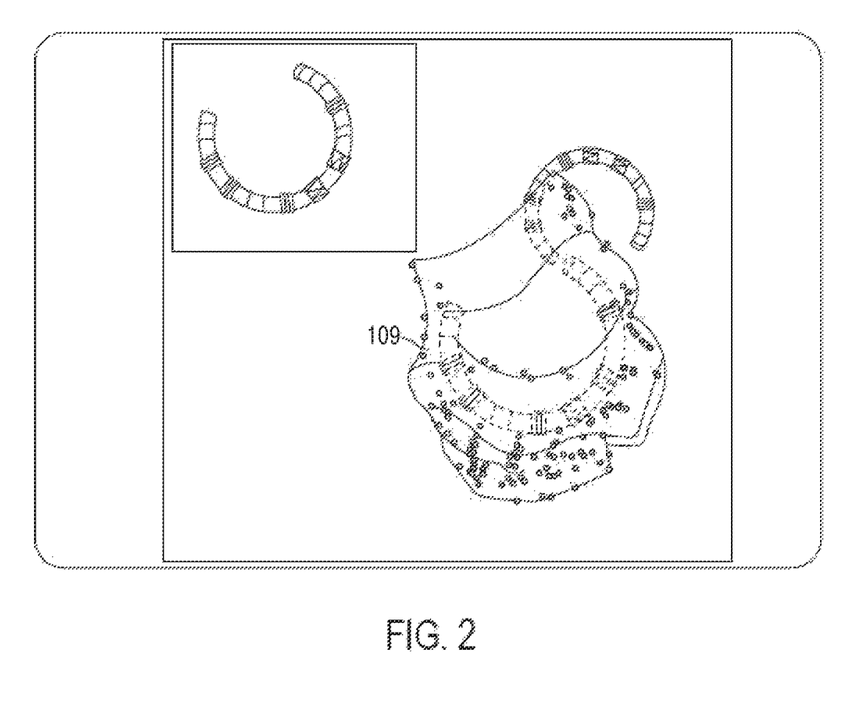
FIG. 2 is a diagram of an example of an organ map that is produced by the system of FIG. 1A, according to aspects of the disclosure.

FIG. 2 shows an example of a functional electro-anatomic map 109 of the patient's heart that is generated by the system 100. In the map 109, local activation times are represented by different shading patterns. Superimposed over the map of the patient's heart is an image of the catheter 120, which shows the orientation of the catheter 120 and the respective positions of the electrodes 122 in the patient's heart.

Figure 3:
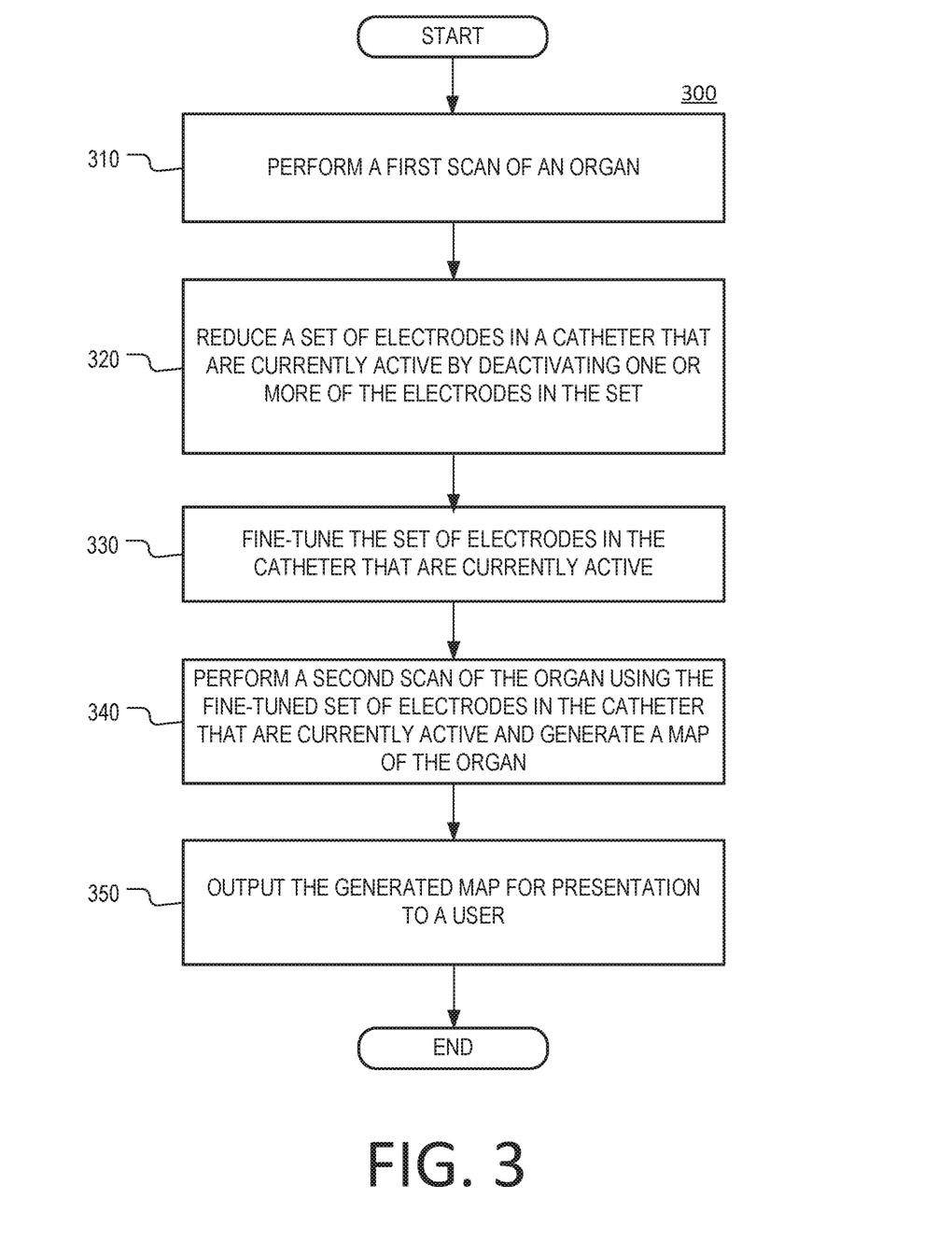
FIG. 3 is a flowchart of an example of a process performed by the system of FIG. 1A, according to aspects of the disclosure.

FIG. 3 is a flowchart of an example of a process for electro-anatomic mapping performed by the processor 112 of the diagnostic device 110, according to aspects of the disclosure.

At step 310, a first scan of an organ is performed using the catheter 120 and a first map of the organ (or portion thereof) is generated. In some implementations, scanning the organ may include obtaining ECG signals from the catheter, and processing those signals in a well-known fashion to produce the first map. In some implementations, the first map may be generated based only on data that is collected using only electrodes that are currently active. The first scan of the organ may be performed using a plurality of electrodes in the catheter that are currently active. In the present example, the organ that is scanned is the heart of patient 103 and the map is of a particular anatomical region in one of the heart chambers.

In some implementations, the set of electrodes that are currently active when the first map is generated may include all electrodes 122 that are available in the catheter 120. Alternatively, in some implementations, the set of electrodes that are currently active when the map is generated may include only some of the electrodes 122. Additionally or alternatively, in some implementations, the processor 112 may generate the first map by retrieving the data structure 180 to identify those electrodes that are currently active before the first scan of the organ is performed. In some implementations, performing the second scan may include identifying one or more of the electrodes 122 that are currently active based on the data structure 180, obtaining one or more signals produced by the electrodes that are currently active, and generating the first map in a well-known fashion, based on the obtained signals.

At step 320, the set of electrodes in the catheter 120 that are currently active is reduced by deactivating one or more of the electrodes that are currently active. The deactivated electrodes may include one or more of:
 (i) one or more electrodes that are not in direct contact with the tissue of the scanned organ;
 (ii) one or more electrodes that are in direct contact with non-conductive areas of the patient's organ (e.g., heart valves or ostium);
 (iii) one or more electrodes that are located further than a threshold distance from any of a plurality of regions of interest in the patient's organ;
 (iv) one or more electrodes that are located further than a threshold distance from a region of interest in the patient's organ.

In some implementations, electrodes that are in direct contact with the tissue of the patient's organ may be identified using a Tissue Proximity Indication (TPI) analysis or signal analysis. TPI, as implemented for example in the CARTO™ system. Additionally or alternatively, in some implementations, electrodes that are located in non-conductive areas of the patient's organ may be identified using signal characterization and model-based mapping. As discussed above, the processor 112 may deactivate a given electrode by updating the data structure 180 to indicate that the electrode is inactive. Additionally or alternatively, the processor 112 may deactivate a given electrode by causing the switching circuitry 125 to interrupt an electrical path between the electrode and the diagnostic device 110 (or connector 121).

At step 330, the set of electrodes in the catheter 120 that are currently active is fine-tuned by performing one or more of:
 (i) activating one or more electrodes that are positioned inside a region of interest in the patient's organ;
 (ii) activating one or more electrodes that are positioned within a threshold distance from a region of interest in the patient's organ;
 (iii) deactivating one or more electrodes that are positioned inside a region of interest in the patient's organ;
 (iv) deactivating one or more electrodes that are positioned within a threshold distance from a region of interest in the patient's organ;
 (v) activating one or more electrodes in the catheter that are not inside or within a threshold distance from any region of interest; and
 (vi) deactivating one or more electrodes in the catheter that are not inside or within a threshold distance from any region of interest).

By way of example, in some implementations, an electrode may be considered to be positioned inside a region of interest of the patient's organ if the electrode is in direct contact with tissue corresponding to the region of interest. Additionally or alternatively, in some implementations, an electrode may be considered positioned within a threshold distance from a region of interest in the patient's organ if the electrode is within a threshold distance from the tissue of the region of interest. According to aspects of the disclosure, in some implementations, the processor 112 may activate a given electrode by modifying the data structure 180 to indicate that the electrode is active. Additionally or alternatively, in some implementations, the processor 112 may activate a given electrode by causing the switching circuitry 125 to close an electrical path connecting the electrode to the diagnostic device 110 and/or the connector 121. Further examples of sub-processes for performing step 330 are provided further below with respect to FIGS. 4-6.

At step 340, a second scan of an organ is performed and a second map of the patient's organ is generated as a result of the second scan. In some implementations, the second map may be generated by the processor 112 using only data that is obtained from electrodes in the catheter that are currently active when the second scan is performed. Additionally or alternatively, in some implementations, the processor may identify the electrodes that are currently active based on the data structure 180.

At step 350, the second map is output for presentation to a user by using the I/O device 114 of the diagnostic device 110. In some implementations, outputting the map may include displaying at least a portion of the map on a display device, such as an LCD monitor. Additionally or alternatively, outputting the second map may include generating an audible signal (e.g., a speech signal or a tone) based on the second map. Additionally or alternatively, in some implementations, outputting the second map may include outputting diagnostic information that is generated based on the second map.

Figure 4:
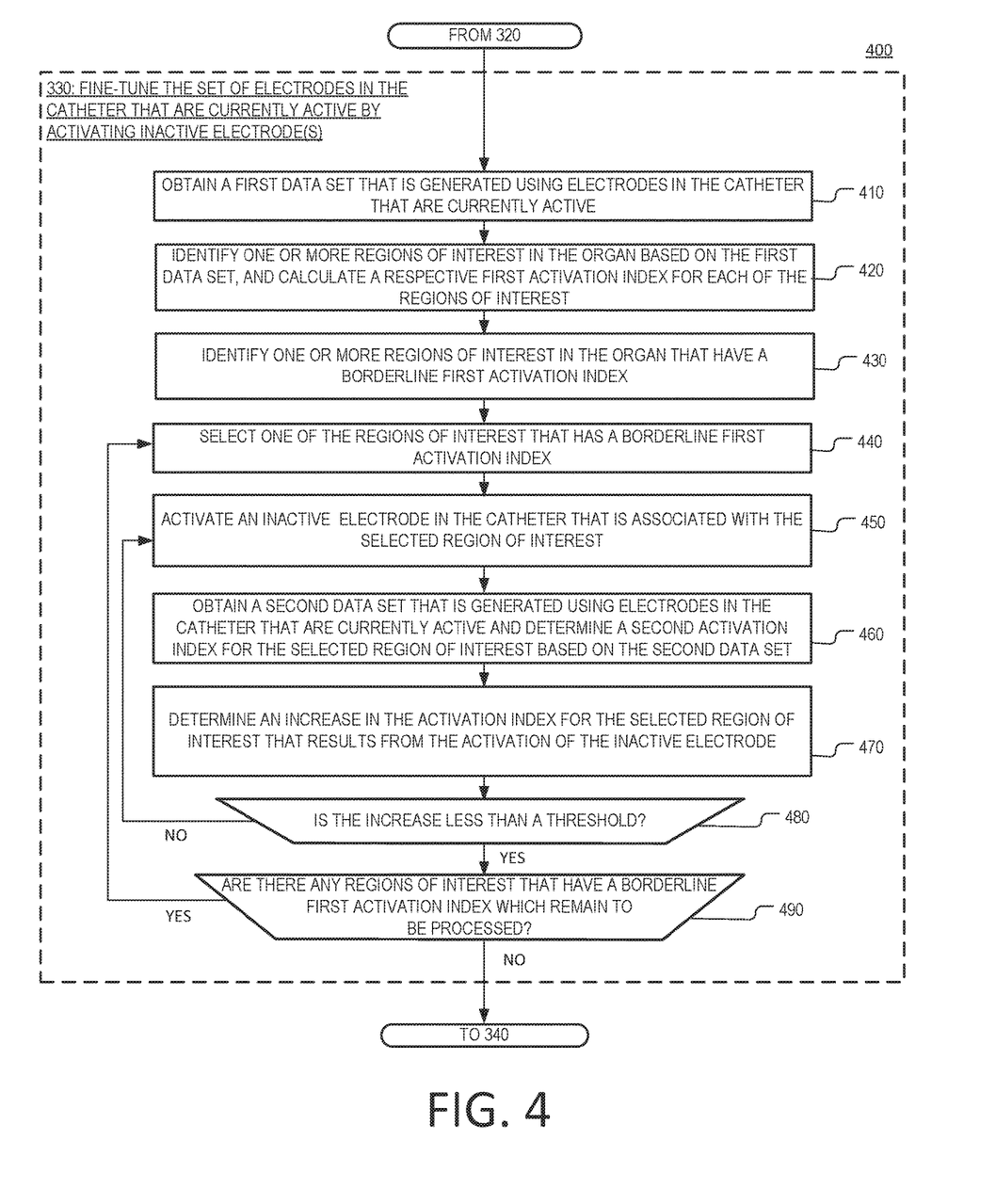
FIG. 4 is a flowchart of an example of a sub-process associated with the process of FIG. 3, according to aspects of the disclosure.

FIG. 4 is a flowchart of an example of a process 400 for fine-tuning the set of electrodes in the catheter 120 that are currently active, as discussed above with respect to step 330 of the process 300.

At step 410, a first data set is obtained using the electrodes in the catheter that are currently active. The first data set may include only data items that are generated by electrodes in the catheter 120 that are currently active. In some implementations, obtaining the first data set may include retrieving from the memory 111 one or more data items that are generated as a result of the first scan discussed with respect to step 310 of the process 300. Additionally or alternatively, in some implementations obtaining the first data set may include retrieving from the memory 111 one or more data items that are generated as a result of another scan that is performed with the catheter 120 after step 320 of the process 300 is executed.

At step 420, one or more regions of interest are identified and an activation index for each of the regions of interest is calculated. In some implementations, respective first activation index for any of the regions of interest may be calculated based on the first data set. Additionally or alternatively, in some implementations, identifying the regions of interest may include performing focal and rotational activation detection to identify areas of stable waves. In general, focal activation may be defined as early consecutive QS waves. Rotational activity may be described as microreentrant circuits of activation. Moreover, rotational activation may be defined as activation patterns which meet criteria including, but not limited to, head to tail distance, CL coverage, and temporal stability. When the detected electrical activation satisfies the algorithm criteria for focal or rotational activation patterns, the areas are marked as regions of interest (ROI). Additionally or alternatively, calculating the activation index for any of the regions of interest when the organ that is scanned is the heart of patient may include calculating the number of heart beats that demonstrates the focal or rotational activity. For example, if focal activation lasts for ten consecutive heart beats, the activation index would equal ten.

At step 430, one or more regions of interest are identified that have borderline first activation indices. According to the present example, any of the first activation indexes may be considered borderline if it falls within a predetermined range.

At step 440, one of the regions of interest having a borderline activation index is selected.

At step 450, a currently-inactive electrode associated with the selected region of interest is activated, thereby increasing the set of electrodes in the catheter 120 that are currently active. In some implementations, the activated electrode may be one that is located within the region of interest. Additionally or alternatively, the activated electrode may be one that is located within a threshold distance of the region of interest. In some implementations, the electrode that is activated may be one that was active when the first map was generated (i.e., an electrode used in generating the first map). Additionally or alternatively, the electrode that is activated may be one that was inactive when the first map was generated (i.e., an electrode not used in generating the first map). According to aspects of the disclosure, in some implementations, the processor 112 may activate the electrode by modifying the data structure 180 to indicate that the electrode is active. Additionally or alternatively, in some implementations, the processor 112 may activate the electrode by causing the switching circuitry 125 to close an electrical path connecting the electrode to the diagnostic device 110 and/or the connector 121.

At step 460, a second data set is obtained using at least the electrodes in the selected region of interest that are currently active, and a second activation index for the region of interest is calculated using the second data set. In some implementations, the second data set may include only data items that are obtained from electrodes in the catheter 120 that are currently active. As can be readily appreciated, the set of electrodes that are currently active when step 460 is performed may include the electrode that is activated at step 450. Additionally or alternatively, in some implementations, unlike the first data set, the second data set may include one or more data items that are generated using the electrode activated at step 450. In some implementations, obtaining the second data set may include retrieving from the memory 111 one or more data items that are generated as a result of a scan that is performed with the catheter 120 after step 450 is executed.

At step 470, an increase in the activation index of the selected region of interest is determined that results from the activation of the electrode at step 460. In some implementations, the increase in the activation index may be determined by subtracting the first activation index of the selected region of interest from the second index of the select region of interest.

At step 480, a determination is made if the increase is less than a threshold. If the increase is less than the threshold, the process 400 returns to step 450, and steps 450-480 are repeated for another electrode that is currently inactive.

At step 490, a determination is made if there are any other regions of interest in the patient's organ that have borderline activation indices and remain to be processed. If there are such regions of interest, the process 400 returns to step 440, and steps 440-490 are repeated for another region of interest in the patient's organ.

Figure 5:
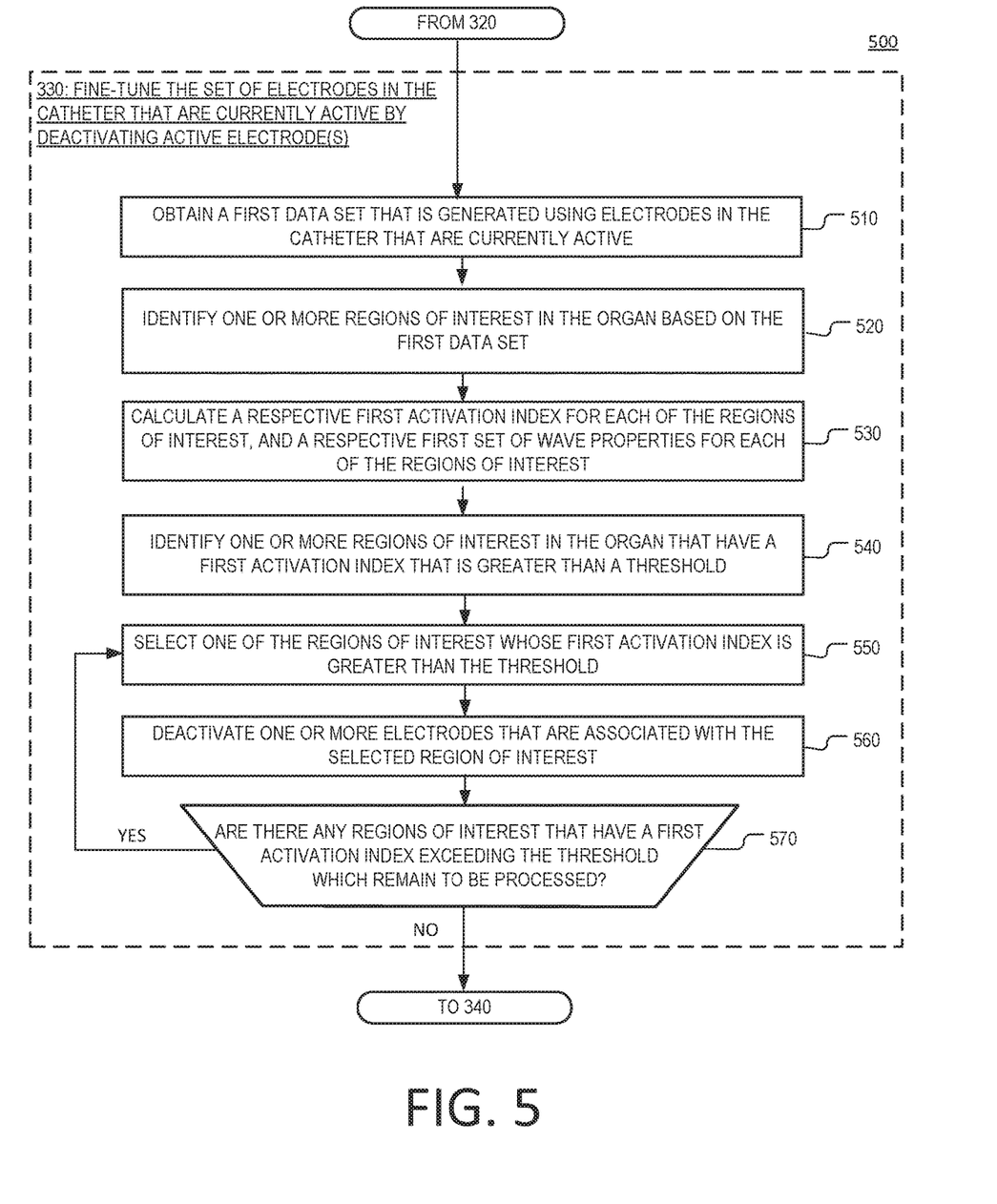
FIG. 5 is a flowchart of an example of a sub-process associated with the process of FIG. 3, according to aspects of the disclosure.

FIG. 5 is a flowchart of an example of a process 500 for fine-tuning the set of electrodes in the catheter 120 that are currently active, as discussed above with respect to step 330 of the process 300.

At step 510, a first data set is obtained using the electrodes in the catheter that are currently active. The first data set may include only data items that are generated by electrodes in the catheter 120 that are currently active. In some implementations, obtaining the first data set may include retrieving from the memory 111 one or more data items that are generated as a result of the first scan discussed with respect to step 310 of the process 300. Additionally or alternatively, in some implementations obtaining the first data set may include retrieving from the memory 111 one or more data items that are generated as a result of another scan that is performed with the catheter 120 after step 320 of the process 300 is executed.

At step 520, one or more regions of interest are identified. In some implementations, each of the selected regions of interest may be identified based on the first data set, as discussed with respect to step 420 of the process 400.

At step 530, a respective first activation index and a respective first set of wave properties are calculated for each of the regions of interest. In some implementations, the respective first activation index and the respective first set of wave properties for any of the regions of interest may be calculated based on the first data set. In some implementations, the plurality of regions of interest may be identified as discussed above with respect to step 420 of the process 400. Additionally or alternatively, in some implementations, the respective first activation index of any of the regions of interest may be identified as discussed above with respect to step 420 of the process 400. Additionally or alternatively, in some implementations, the respective first set of wave properties of any of the regions of interest may include parameters including, but not limited to, conduction velocity, special morphology sequence, and special morphology shape.

At step 540, one or more regions of interest are identified that have respective first indices that are greater than an activation index threshold.

At step 550, one of the regions of interest is selected that has an activation index that is greater than the activation index threshold.

At step 560, one or more active electrodes associated with the selected region of interest are deactivated. Step 560 is discussed further below with respect to FIG. 6.

At step 570, a determination is made if there are any other regions of interest in the patient's organ whose activation indices exceed the activation index threshold, and which remain to be processed. If there are such electrodes, the process 500 returns to step 550, and steps 550-570 are repeated for another region of interest in the patient's organ.

Figure 6:
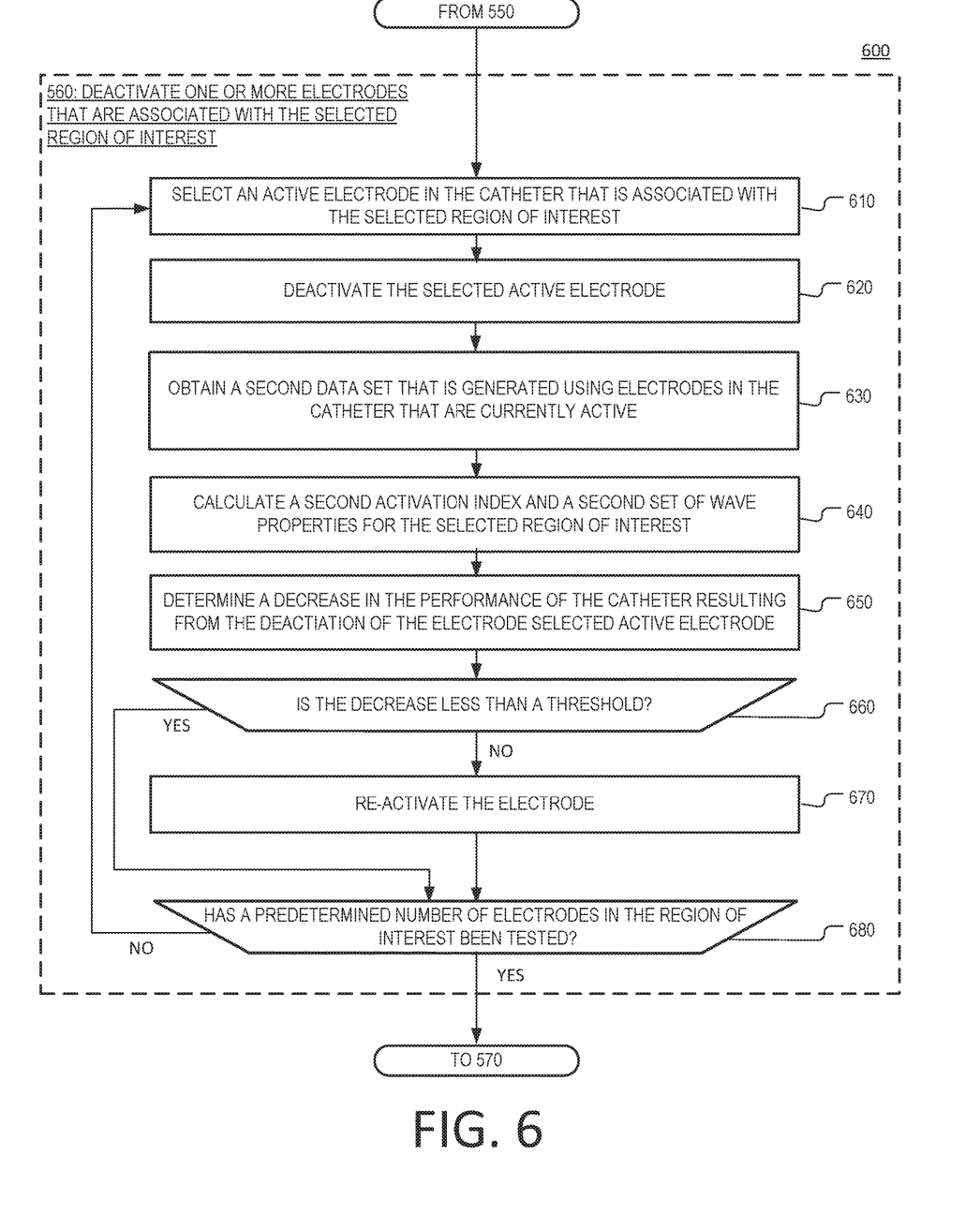
FIG. 6 is a flowchart of an example of a sub-process associated with the process of FIG. 5.

FIG. 6 is a flowchart of an example of a process 600 for identifying and deactivating electrodes that are associated with a selected region of interest, as discussed with respect to step 560 of the process 500. In some implementations, executing the process 600 may result in electrodes associated with the selected region of interest that have the least effect on the operation of the catheter 120 becoming deactivated.

At step 610, an electrode in the catheter 120 that is currently active is selected. The selected electrode may be one that is associated with the particular region of interest. More particularly, in some implementations, the electrode may be one that is located in the selected region of interest. Additionally or alternatively, in some implementations, the electrode may be one that is located within a predetermined distance from the selected region of interest.

At step 620, the selected electrode is deactivated. In some implementations, deactivating the selected electrode may include updating the data structure to indicate the selected electrode is inactive. As discussed above, the processor 112 may deactivate a given electrode by updating the data structure 180 to indicate that the electrode is inactive. Additionally or alternatively, the processor 112 may deactivate a given electrode by causing the switching circuitry 125 to interrupt an electrical path between the electrode and the diagnostic device 110 (or connector 121).

At step 630, a second data set is obtained using at least the electrodes in the selected region of interest that are currently active. In some implementations, the second data set may include only data items that are generated by electrodes in the catheter that are currently active. As a result, unlike the first data set, the second data set may not include data items generated by the electrode that is deactivated at step 620.

At step 640, a second activation index and a second set of wave properties are calculated for the selected region of interest based on the second data set. In some implementations, the respective first activation index of any of the regions of interest may be identified as discussed above with respect to step 420 of the process 400. The respective first set of wave properties of any of the regions of interest may include at least one of conduction velocity of propagation action potential impulse(s) across the tissue of the selected region of interest, and/or direction of propagation of the action potential impulse(s).

At step 650, a decrease in the performance of the catheter 120 is determined that results from the deactivation of the electrode at step 650. In some implementations, the decrease in performance may be determined based on a metric that is calculated using at least some of the first activation index of the region of interest, the first set of wave properties of the region of interest, the second activation index of the selected region of interest, the second set of wave properties of the selected region of interest. The metric may be a number, a string, and/or any other suitable type of alphanumerical string. In some implementations, the metric may be determined based on one or more of:
  (i) a difference between the first activation index and the second activation index of the selected region of interest;
  (ii) a difference between the first set of wave properties and the second set of wave properties of the selected region of interest;
  (iii) a difference between wave propagation velocity of the selected region of interest prior to the electrode being deactivated and the wave propagation velocity of the selected region of interest after the electrode is deactivated; and
  (iv) a difference between wave propagation direction of the selected region of interest prior to the electrode being deactivated and the wave propagation direction of the selected region of interest after the electrode is deactivated.

Additionally or alternatively, in some implementations the metric may be determined by using a fuzzy logic algorithm to compare the first activation index and the first set of wave properties of the selected region of interest to the second activation index and the second set of wave properties of the selected region of interest.

At step 660, a determination is made whether the decrease in the performance is less than a threshold. In some implementations, the determination may be made by the processor 112 comparing the metric calculated at step 650 to a threshold value that is pre-stored in the memory 111. If the decrease in performance is greater than a threshold, the process proceeds to step 670. Otherwise, the process proceeds to step 680.

At step 670, the electrode that is deactivated at step 640 is re-activated. According to aspects of the disclosure, in some implementations, the processor 112 may activate the electrode by modifying the data structure 180 to indicate that the electrode is active. Additionally or alternatively, in some implementations, the processor 112 may activate the electrode by causing the switching circuitry 125 to close an electrical path connecting the electrode to the diagnostic device 110 and/or the connector 121.

At step 680, a determination is made whether a predetermined number of electrodes associated with the region of interest have been tested. The predetermined number of electrodes may include all electrodes that are located in the region of interest, and/or any other suitable number of electrodes that are located within a predetermined distance from the region of interest. If the predetermined number of electrodes have been tested, the process 600 ends. Otherwise, the process 600 returns to step 610 and steps 610-680 are repeated for another electrode in the selected region of interest.

Although in the example of the process 600, only one electrode is deactivated/re-activated during each iteration, alternative implementations are possible in which multiple electrodes are deactivated/re-activated. Furthermore, it will be understood that the process 600 is provided only as an example of many possible ways for identifying electrodes in a region of interest that have the least effect on the performance of a catheter and deactiating those electrodes.

For example, in some implementations, the electrodes in the selected region of interest that are deactivation may be selected by: (i) identifying a plurality of different sets of electrodes in the selected region of interest, each set of electrodes including one or more electrodes, (ii) determining the effect which disabling each set of electrodes has on the performance of the catheter 120, (iii) selecting one of the electrode sets based on the effect which its deactivation has on the performance of the catheter 120, and (iv) deactivating the selected set of electrodes. In some implementations, the selected set of electrodes may be the largest set of electrodes which when disabled allows the performance of the catheter to remain above a performance threshold. In some implementations, the effect which disabling each of the sets of electrodes has on the performance of the catheter may be performed by deactivating each set of electrodes, determining the effect which disabling the set of electrodes has on the performance of the catheter 120, and reactivating the deactivated set of electrodes to test another one of the sets. The effect which disabling a particular set of electrodes has on the operation of the catheter may be determined as discussed with respect to step 650 of the process 600.

FIGS. 1A-6 are provided as an example only. At least some of the elements discussed with respect to these figures can be arranged in different order, combined, and/or altogether omitted. It will be understood that the provision of the examples described herein, as well as clauses phrased as "such as," "e.g.", "including", "in some aspects," "in some implementations," and the like should not be interpreted as limiting the disclosed subject matter to the specific examples.

The methods or flow charts provided herein can be implemented in a computer program, software, or firmware incorporated in a non-transitory computer-readable storage medium for execution by a general-purpose computer or a processor. Examples of non-transitory computer-readable storage mediums include a ROM, a random-access memory (RAM), a register, cache memory, semiconductor memory devices, magnetic media such as internal hard disks and removable disks, magneto-optical media, and optical media such as CD-ROM disks, and digital versatile disks (DVDs).

Having described the invention in detail, those skilled in the art will appreciate that, given the present disclosure, modifications may be made to the invention without departing from the spirit of the inventive concepts described herein. Therefore, it is not intended that the scope of the invention be limited to the specific embodiments illustrated and described.

What is claimed is:

1. A method comprising:
    providing an output device configured to output a map of a heart;
    providing at least one processor operatively coupled to the output device;
    providing a memory configured to store a data structure configured to identify a list of electrodes that are currently active or inactive;
    providing an intracardiac catheter configured for intracardiac ablations and intracardiac mapping;
    performing a first scan of the heart using a set of electrodes in the catheter that are currently active;
    deactivating one or more of the electrodes in the set based on data that is collected as a result of the first scan;
    detecting an electrical activation in the heart that falls within a criteria for a focal or rotational activation pattern;
    identifying a region of interest in the heart having the detected electrical activation;
    calculating an activation index for the region of interest, the activation index comprising a predetermined range for a number of heart beats that demonstrates the focal or rotational activation pattern;
    tuning the set by at least one of (i) deactivating one or more electrodes associated with the region of interest in the set that remain active after the deactivating, and (ii) activating one or more electrodes associated with the region of interest in the catheter that are inactive;
    performing a second scan of the heart using electrodes in the set that are currently active after the tuning is performed, and generating the map of the heart based on data collected as a result of the second scan; and
    outputting the map of the heart for presentation to a user, wherein the at least one processor retrieves the data structure from the memory to determine which of the one or more electrodes in the catheter are currently active;
    wherein the at least one processor activates or deactivates the one or more electrodes by modifying the data structure; and
    wherein signals from currently active electrodes are used to generate the map while signals from currently inactive electrodes are not used to generate the map.

2. The method of claim 1, wherein tuning the set further includes:
    activating a first electrode in the catheter when activating the first electrode causes the activation index of the region of interest to be increased.

3. The method of claim 2, further comprising:
    detecting an increase in the activation index of the region of interest that results from the first electrode in the catheter being activated; and
    activating a second electrode in the catheter based on whether the increase in the activation index is less than a threshold.

4. The method of claim 1, wherein tuning the set includes deactivating a selected first electrode in the catheter that is associated with a region of interest, the first electrode being selected based on an impact which the first electrode has on performance of the catheter with respect to the region of interest.

5. The method of claim 4, wherein the first electrode is one that is in direct contact with tissue corresponding to the region of interest or one that is within a predetermined distance from the tissue corresponding to the region of interest.

6. The method of claim 1, wherein the heart is a heart.

7. The method of claim 1, wherein deactivating the one or more of the electrodes in the set based on data that is collected as a result of the first scan includes deactivating one or more electrodes that are not in physical contact with tissue of the heart that is part of one or more regions of interest in the heart.

8. The method of claim 1, wherein deactivating the one or more of the electrodes in the set based on data that is collected as a result of the first scan includes deactivating one or more electrodes that are associated with one or more non-conductive regions of the heart.

9. The method of claim 1, wherein tuning the set includes reducing the set by deactivating one or more electrodes in the catheter that are currently active based on a wave property of a region of interest in the heart, the wave property including velocity of propagation of action potential impulses across the region of interest.

10. The method of claim 1, wherein tuning the set includes reducing the set by deactivating one or more electrodes in the intracardiac catheter that are currently active based on a wave property of a region of interest in the heart, the wave property including direction of propagation of action potential impulses across the region of interest.

11. A diagnostic device, comprising:
an intracardiac catheter configured for intracardiac ablations and intracardiac mapping;
an output device;
a memory configured to store a data structure identifying a list of electrodes that are currently active or inactive; and
at least one processor operatively coupled to the output device, the at least one processor being configured to:
perform a first scan of a heart using a set of electrodes in the catheter that are currently active;
deactivate one or more of the electrodes in the set based on data that is collected as a result of the first scan;
detect an electrical activation in the heart that falls within a criteria for a focal or rotational activation pattern;
identify a region of interest in the heart having the detected electrical activation;
calculate an activation index for the region of interest, the activation index comprising a predetermined range for a number of heart beats that demonstrates the focal or rotational activation pattern;
tune the set by at least one of (i) deactivating one or more electrodes associated with the region of interest in the set that remain active after the deactivating, and (ii) activating one or more electrodes associated with the region of interest in the catheter that are inactive;
perform a second scan of the heart using electrodes in the set that are currently active after the tuning is performed, and generating a map of the heart based on data collected as a result of the second scan; and
output the map of the heart using the output device,
wherein the at least one processor retrieves the data structure from the memory to determine which of the one or more electrodes in the catheter are currently active;
wherein the at least one processor activates or deactivates the one or more electrodes by modifying the data structure; and
wherein signals from currently active electrodes are used to generate the map while signals from currently inactive electrodes are not used to generate the map.

12. The diagnostic device of claim 11, wherein tuning the set includes:
activating a first electrode in the catheter when activating the first electrode causes the activation index of the region of interest to be increased.

13. The diagnostic device of claim 12, further comprising:
detecting an increase in the activation index of the region of interest that results from the first electrode in the catheter being activated; and
activating a second electrode in the catheter based on whether the increase in the activation index is less than a threshold.

14. The diagnostic device of claim 11, wherein tuning the set includes deactivating a selected first electrode in the catheter that is associated with a region of interest, the first electrode being selected based on an impact which the first electrode has on performance of the catheter with respect to the region of interest.

15. The diagnostic device of claim 14, wherein the first electrode is one that is in direct contact with tissue corresponding to the region of interest or one that is within a predetermined distance from the tissue corresponding to the region of interest.

16. The diagnostic device of claim 11, wherein the heart is a heart.

17. The diagnostic device of claim 11, wherein deactivating the one or more of the electrodes in the set based on data that is collected as a result of the first scan includes deactivating one or more electrodes that are not in physical contact with tissue of the heart that is part of one or more regions of interest in the heart.

18. The diagnostic device of claim 11, wherein deactivating the one or more of the electrodes in the set based on data that is collected as a result of the first scan includes deactivating one or more electrodes that are associated with one or more non-conductive regions of the heart.

19. The diagnostic device of claim 11, wherein tuning the set includes reducing the set by deactivating one or more electrodes in the catheter that are currently active based on a wave property of a region of interest in the heart, the wave property including velocity of propagation of action potential impulses across the region of interest.

20. The diagnostic device of claim 11, wherein tuning the set includes reducing the set by deactivating one or more electrodes in the catheter that are currently active based on a wave property of a region of interest in the heart, the wave property including direction of propagation of action potential impulses across the region of interest.

* * * * *

UNITED STATES PATENT AND TRADEMARK OFFICE
CERTIFICATE OF CORRECTION

| | |
|---|---|
| PATENT NO. | : 10,912,484 B2 |
| APPLICATION NO. | : 16/030358 |
| DATED | : February 9, 2021 |
| INVENTOR(S) | : Morris Ziv-Ari et al. |

It is certified that error appears in the above-identified patent and that said Letters Patent is hereby corrected as shown below:

In the Drawings
In Fig. 6, Sheet 9 of 9, Tag "650", Line 2, delete "DEACTIATION" and insert
-- DEACTIVATION --, therefor.

In the Specification
In Column 3, Line 59, delete "is schematic" and insert -- is a schematic --, therefor.
In Column 8, Line 25, delete "the select" and insert -- the selected --, therefor.
In Column 11, Line 3, delete "deactiating" and insert -- deactivating --, therefor.

Signed and Sealed this
Seventh Day of February, 2023

Katherine Kelly Vidal
*Director of the United States Patent and Trademark Office*